United States Patent
Gorges et al.

(10) Patent No.: US 11,564,654 B2
(45) Date of Patent: Jan. 31, 2023

(54) METHOD AND SYSTEM FOR CALIBRATING AN X-RAY IMAGING SYSTEM

(71) Applicant: THALES, Courbevoie (FR)

(72) Inventors: Sébastien Gorges, Saint Jean de Moirans (FR); Guillaume Bernard, Moirans (FR); Yannick Grondin, Meylan (FR)

(73) Assignee: THALES, Courbevoie (FR)

( * ) Notice: Subject to any disclaimer, the term of this patent is extended or adjusted under 35 U.S.C. 154(b) by 88 days.

(21) Appl. No.: 16/958,894

(22) PCT Filed: Dec. 28, 2018

(86) PCT No.: PCT/EP2018/097126
§ 371 (c)(1),
(2) Date: Jun. 29, 2020

(87) PCT Pub. No.: WO2019/129879
PCT Pub. Date: Jul. 4, 2019

(65) Prior Publication Data
US 2020/0337670 A1    Oct. 29, 2020

(30) Foreign Application Priority Data
Dec. 28, 2017 (FR) ........................................ 1701389

(51) Int. Cl.
*A61B 6/00* (2006.01)
*A61B 90/00* (2016.01)

(52) U.S. Cl.
CPC .............. *A61B 6/583* (2013.01); *A61B 6/488* (2013.01); *A61B 90/39* (2016.02); *A61B 6/4441* (2013.01);
(Continued)

(58) Field of Classification Search
CPC .......... A61B 6/583; A61B 6/488; A61B 90/39; A61B 6/4441; A61B 2090/3916;
(Continued)

(56) References Cited

U.S. PATENT DOCUMENTS 6,049,582 A    4/2000 Navab
6,320,928 B1   11/2001 Vaillant et al.
(Continued)

FOREIGN PATENT DOCUMENTS

EP    2 868 277 A1    5/2015
EP    3 141 187 A1    3/2017

OTHER PUBLICATIONS

Madan, et al., "Device and methods for gold standard registration of clinical 3D and 2D cerebral angiograms", Progress in Biomedical Optics and Imaging, vol. 9415, Mar. 18, 2015.
(Continued)

*Primary Examiner* — Marcus H Taningco
(74) *Attorney, Agent, or Firm* — BakerHostetler

(57) ABSTRACT

A method for calculating during use the geometric parameters of an x-ray imaging system, an object or a patient to be observed being placed between the x-ray source and a detector of x-rays having passed through the object or patient, wherein it includes at least the following steps: detecting at least one marker on the object or the patient or in proximity to the object, the marker being of unknown 3D position, acquiring a plurality of 2D images for a plurality of viewpoints of the imaging system, detecting the position of at least one marker in each of the acquired 2D images, estimating the projection matrices corresponding to the projections of the object at various viewing angles and reconstructing in 3D the position of a marker on the basis of the estimation of the projection matrices.

12 Claims, 2 Drawing Sheets

(52) U.S. Cl.
CPC ............... *A61B 2090/3916* (2016.02); *A61B 2090/3966* (2016.02); *A61B 2090/3991* (2016.02)

(58) Field of Classification Search
CPC .... A61B 2090/3966; A61B 2090/3991; A61B 6/5205
See application file for complete search history.

(56) References Cited

U.S. PATENT DOCUMENTS

| | | |
|---|---|---|
| 6,510,241 B1 | 1/2003 | Vaillant et al. |
| 2002/0044631 A1 | 4/2002 | Graumann et al. |
| 2005/0027193 A1* | 2/2005 | Mitschke ............... A61B 34/20 600/427 |
| 2008/0192884 A1* | 8/2008 | Ritter .................... A61B 6/584 378/4 |
| 2010/0284601 A1 | 11/2010 | Rubner et al. |
| 2011/0004431 A1* | 1/2011 | Ringholz ............. A61B 6/4441 702/94 |
| 2017/0238897 A1 | 8/2017 | Siewerdsen et al. |
| 2019/0000564 A1* | 1/2019 | Navab .................... G06T 7/521 |

OTHER PUBLICATIONS

Triggs, et al., "Bundle adjustment—a modern synthesis", HAL Id: inria-00590128 https://hal.inria.fr/inria-00590128—Submitted on May 3, 2011.

\* cited by examiner

METHOD AND SYSTEM FOR CALIBRATING AN X-RAY IMAGING SYSTEM

CROSS-REFERENCE TO RELATED APPLICATIONS

This application is a National Stage of International patent application PCT/EP2018/097126, filed on Dec. 28, 2018, which claims priority to foreign French patent application No. FR 1701389, filed on Dec. 28, 2017, the disclosures of which are incorporated by reference in their entirety.

FIELD OF THE INVENTION

The invention relates to a method and a system for determining, during operation, the geometrical features of a system for reconstructing a three-dimensional (3D) image from images acquired by an X-ray imaging system. The invention thus allows online calibration of an X-ray imaging system.

BACKGROUND

The geometrical features are estimated during the rotational acquisition of a C-arm device.

It is common to use a mobile radiology system to perform surgical or interventional procedures. These systems, also called mobile C-arms (or block amplifier), allow the surgeon to acquire X-ray images during the intervention and to monitor the position of the tools (catheter, needle, prosthesis, etc.) that are used by the surgeon in real time in a way that is as non-invasive as possible. The majority of these systems make it possible to obtain two-dimensional images with a video image stream of thirty images per second. The practitioner then uses these images to mentally reconstruct the morphology of the patient in order to position the tool precisely in the area to be operated on, in real time. More recently, more sophisticated systems have emerged and make it possible to acquire a 3D image of the tool that is used by a surgeon during an intervention. The radiology system performs a rotation about the patient for the purpose of obtaining a set of two-dimensional 2D images. These 2D images are then processed by a reconstruction algorithm, allowing a 3D volume image to be obtained. In order to reconstruct the image, the algorithm needs to know, for each 2D image, the exact geometry of the C-arm, that is to say the position of the detector and of the X-ray source with respect to the patient. The systems used at present propose to calibrate the C-arm offline during preventative maintenance phases of the device, every six months or every year.

U.S. Pat. No. 6,510,241 describes a method for calibrating a radiology apparatus, wherein a virtual volume surrounding the object to be imaged is generated and broken down into voxels (3D pixels). The method comprises a step of acquiring the set of numbered projected two-dimensional images and the three-dimensional image is reconstructed from the projected image.

U.S. Pat. No. 6,320,928 describes an image reconstruction method in which a plurality of two-dimensional digital images of an object are acquired for various positions of a camera revolving around the object. The projected images are calibrated in a volume containing the object and divided into voxels whose spatial coordinates are identified in a chosen calibration reference frame.

U.S. Pat. No. 6,049,582 relates to a C-arm device calibration method for a 3D reconstruction in an imaging system comprising an imaging source and an imaging plane, which uses a planar transformation to link the voxels in a voxel space and pixels in the imaging plane.

Patent application EP3141187 relates to a calibration chart for geometrically calibrating an X-ray imaging device intended to generate three-dimensional images of an object through reconstruction based on two-dimensional projections of said object. The calibration chart comprises a volume support equipped with markers having a radiological absorbance that provides contrast with respect to the volume support, the markers being distributed in a three-dimensional pattern. The markers are distributed into subsets of markers that are distributed in respective substantially parallel straight lines such that sequences of cross-ratios are able to be constructed from the respective subsets of markers. Each sequence of cross-ratios comprises a single cross-ratio for each quadruplet of markers in which the markers are ordered in an order depending on the rank numbers of the respective markers along the straight line on which they are aligned, in a first predefined direction, said order being common to all of the cross-ratios, and when a subset of markers comprises at least five markers, the order of the cross-ratios in the respective sequences of cross-ratios follows a predefined rule common to all of the sequences of cross-ratios.

These systems assume that the rotational acquisition is reproducible enough for the geometry, determined "offline", of the C-arm to be applicable to the images acquired during a surgical intervention.

The mechanics of the systems have been improved in order to stabilize the arch during the rotational acquisition of the 2D images. However, these improvements (reduction in mechanical play, use of stiffer components, etc.) lead to more burdensome devices. In addition, it is not always a simple matter to make modifications to existing devices.

Other methods from the prior art propose an online calibration.

A first method is based on the use of markers. A calibration chart is positioned on or next to a patient during the intervention. This makes it possible to precisely estimate the geometry of the device online, without having to worry about the reproducible nature of the measurement conditions. Patent application US 201000284601 describes such a method.

However, the methods known from the prior art that use a chart are not optimum in the context of surgical use or other applications having equivalent usage constraints, for the reasons explained below:

The chart has to be produced precisely in order that the 3D position of the points is known with precision, which represents a cost, The chart itself may be bulky and difficult to use when the patient is present, The chart should have to be sterilized, since it is used in a sterile environment, and has to undergo a chemical/thermal treatment before and after it is used.

A second type of image reconstruction method is based on using an image. These methods make use of the anatomical content of an image in order to perform both a 3D image reconstruction and a geometrical calibration.

In patent EP2868277, the method uses markers, but the 3D positions of the markers have to be known precisely in order to determine the geometrical parameters.

SUMMARY OF THE INVENTION

The invention is based on a novel approach using self-adhesive markers without having to know the 3D position of the markers.

The invention relates to a method for calculating, during operation, the geometrical parameters of an X-ray imaging system, an object or a patient to be observed being positioned between the X-ray source and an X-ray detector detecting X-rays that have passed through the object or the patient, characterized in that it comprises at least the following steps:

Using at least one marker, the marker initially having an unknown 3D position,

Acquiring a plurality of 2D images for a plurality of viewpoints of the imaging system, Detecting the position of at least one marker in each of the acquired 2D images, Estimating the projection matrices corresponding to the projections of the object at different viewing angles and reconstructing the position of a marker in 3D from the estimation of the projection matrices.

The method may comprise an offline calibration step in order to initially calculate the calibration matrices used in the final step of determining the geometry parameters.

In another variant, the initial projection matrices are calculated using the orientation sensors or the positioning sensors of the system.

The markers may be inserted or contained in patches that are positioned on or close to the patient or the object, and the patches that are used are for example adhesive patches defined as follows:

An adhesive tape that will be affixed to an object or a patient,

A set of radio-opaque markers distributed over the surface of the patch,

A fluid-resistant outer surface.

It is possible to distribute the markers on a patch so as to cover the entire surface of the patch.

Another possibility consists in using small markers distributed over the entirety of a compressive garment before covering the area to be reconstructed.

Another variant consists in using one or more anatomical markers or else in using radio-opaque markers implanted in the patient's anatomy, for example in a bone.

The method may comprise a step of using the geometrical features of the system to reconstruct a 3D image.

BRIEF DESCRIPTION OF THE DRAWINGS

Other features and advantages of the present invention will become more clearly apparent upon reading the description of exemplary embodiments provided by way of completely non-limiting illustration alongside the appended figures, in which.

DETAILED DESCRIPTION

Figure 1:
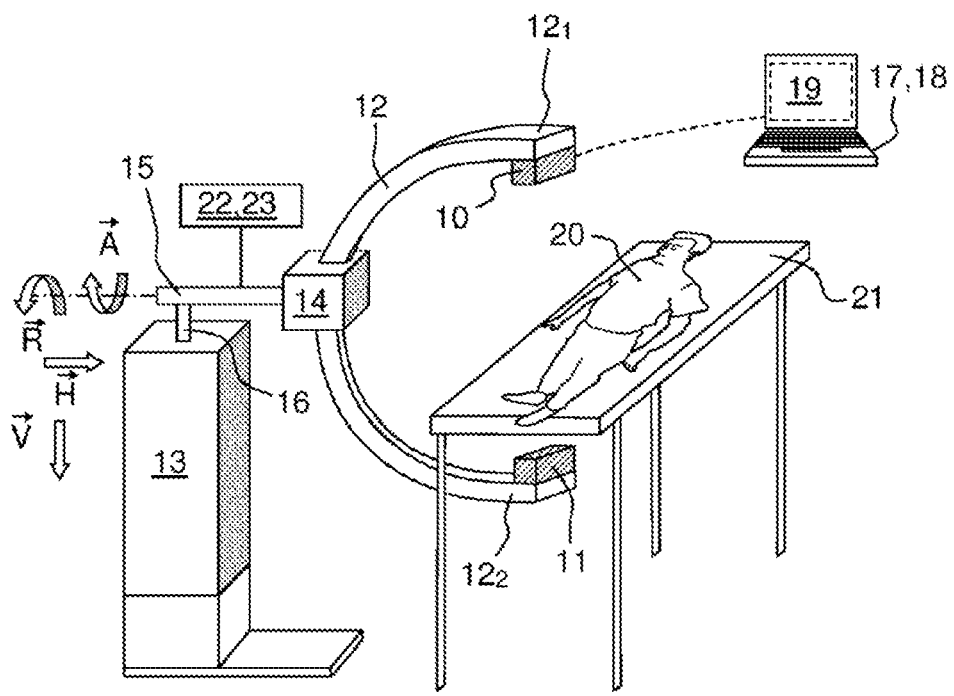
FIG. 1 shows a diagram showing a patient in position.

FIG. 1 illustrates an example of a device allowing a practitioner to track, in real time, the position of a tool that he is using during a surgical intervention. The device comprises an imaging system comprising an X-ray source 10 and an X-ray detector 11. The device consists of an arch 12 or C-arm supporting the X-ray source at a first end $12_1$ and the X-ray detector at a second end $12_2$. The arch or C-arm 12 is held on a frame 13 by a holding part 14.

A horizontal guide 15 attached to the frame 13 via a vertical part 16 and to the holding part 14 of the arch allows the arch to move horizontally in translation, arrow $\vec{H}$.

The holding part 14 allows the C-arm 12 to perform an "orbital rotation" movement along the arrow $\overline{R}$.

The rotation of the part 14 and of the arch is reflected by an angular rotation along the arrow $\overline{A}$.

The vertical movement is created by the horizontal translational movement of the guide and of the vertical part.

The seals that are used between the various elements of the system allowing the abovementioned rotational movements are known to a person skilled in the art and will not be described. Likewise, the abovementioned movements of the radiology system are known to a person skilled in the art.

The device also comprises a processing device 17 comprising a processor 18 configured to execute the steps of the method according to the invention, in order to determine the geometrical features of the device during the intervention by the surgeon. The device may comprise a screen 19 on which the surgeon is able to view the position of the tool in real time.

The device is also equipped with orientation sensors 22 or positioning sensors 23.

Figure 2:
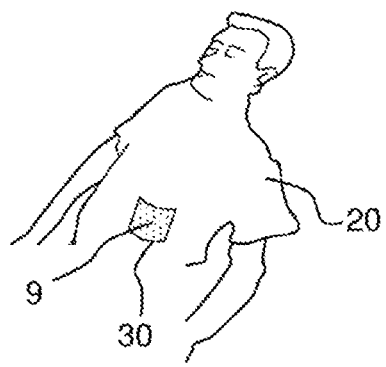
FIG. 2 shows an example of a patch positioned on the patient.

A patient 20 is positioned on an operating table 21. FIG. 2 outlines one exemplary implementation of the method in which the markers are incorporated or integrated into a patch.

The patch 30 is positioned in the upper part of the body and comprises at least one marker q. The coordinates of the patch or the position of the patches are not known initially. It is possible to use one or more patches to implement the method according to the invention.

Figure 3:
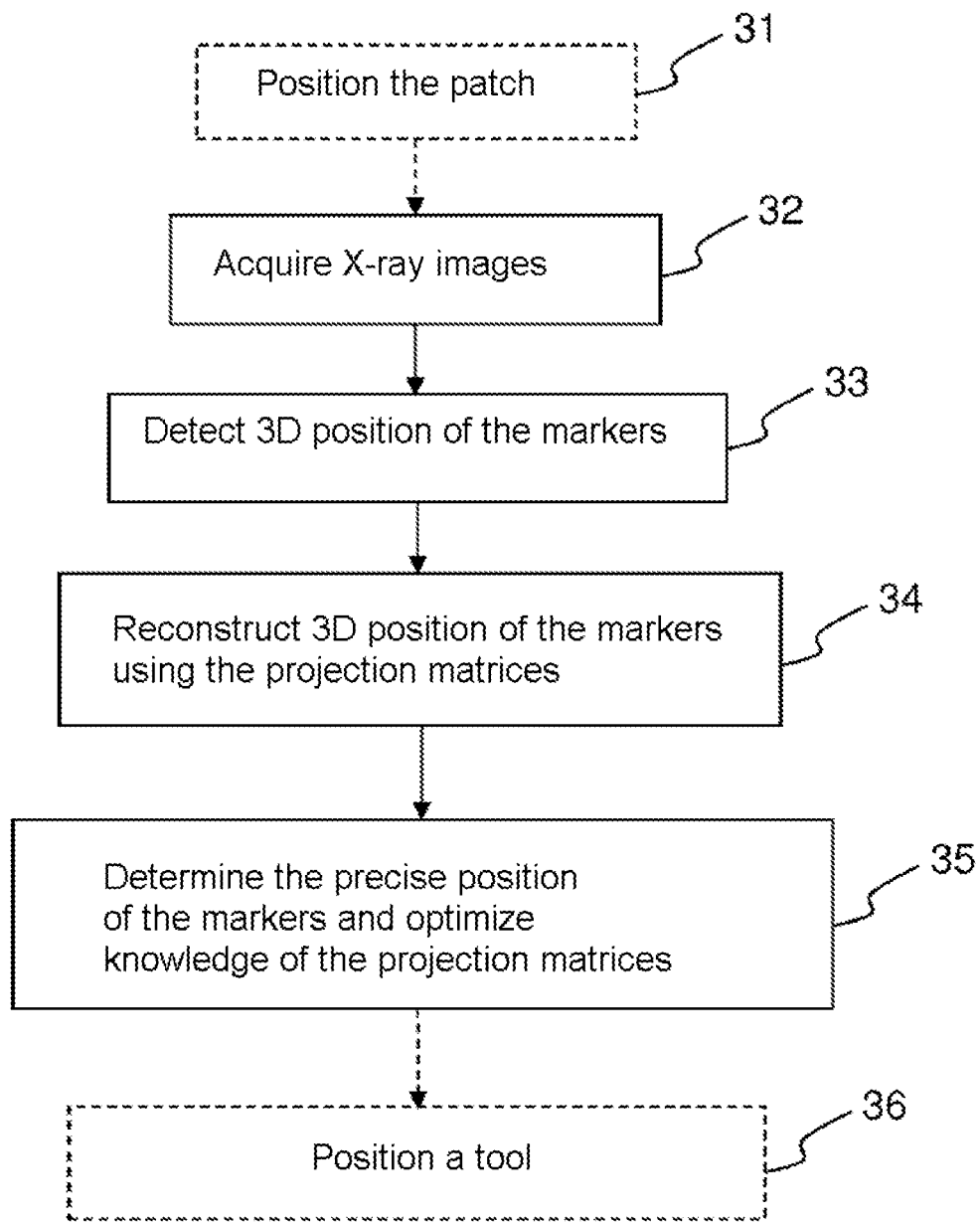
FIG. 3 shows a sequence of steps implemented by the method according to the invention.

FIG. 3 illustrates an example of a sequence of steps implemented by the method according to the invention, in the case in which the markers are integrated into a patch.

Step 1

One or more patches 30 incorporating radio-opaque markers are affixed to the skin of the patient or of the object 20, for example close to an area to be operated on, 31. This will allow the practitioner to precisely obtain a reconstruction of the organ on which he has to operate.

Step 2

A plurality of 2D images are acquired for various viewpoints in order to perform a 3D reconstruction, 32. The X-ray source and the detector are moved around the body 20 to be imaged so as to perform a plurality of projections of the body at different viewing angles. The projections that are thus performed will be used to reconstruct a three-dimensional image of the imaged body.

Step 3

The radio-opaque markers contained in the patch 30 are detected in each 2D image acquired at the X-ray detector and are paired from one image to another, 33. Geometrical or radiometric similarity criteria are used to pair the markers.

Step 4

A 3D reconstruction of the markers is performed using a first estimation of the projection matrices, 34. These projection matrices Mi may be determined during a preliminary offline calibration or predicted based on the position sensors of the system. These 4*3 projection matrices make it possible to match each point of the object or of the patient in the 3D space, for example with respect to the terrestrial reference frame, with its projection onto a planar 2D detector linked to the detector.

At the end of this pairing step, a first estimation of the 3D position of the markers is obtained.

Step 5

The 3D position of the markers and the knowledge of the projection matrices are then iteratively fine-tuned, 35. The geometrical parameters, specifically the projection matrices and the 3D position of the markers, are estimated jointly while minimizing the criterion set forth below.

Let there be a set of N projections and therefore of N matrices to be determined. Let there be a set of L points to be reconstructed, and the criterion is given by:

$$X, M = \mathrm{argmin} \sum_{i=1}^{N} \sum_{j=1}^{L} \|M_i X_j - q_{ij}\|$$

where $q_{ij}$ denotes the 2D coordinates of a marker numbered j detected in an image i obtained by the system, X is the set of L 3D points to be reconstructed, $X_j$ is the point numbered j, M is the set of N projection matrices, $M_i$ is the projection matrix of the image i.

At the end of this step 35, it is possible to precisely reconstruct the corresponding 3D image.

The 3D images thus obtained may be used to allow a practitioner to precisely position his tools during an operation, 36.

The general principle of bundle adjustment methods is described in the document entitled "Bundle adjustment—a modern synthesis" by B.trigs, P F Mc Lauchlan, R I Hartley, International Workshop on Vision Algorithms, Corfu, Greece, Sep. 21-22, 1999 Proceedings.

Any other algorithm taking the coordinates of a marker as determined by executing the method at input in order to deduce the geometrical parameters of the device therefrom may be used.

According to one variant embodiment, the method comprises a preliminary offline calibration step that leads to imprecise geometry of the C-arm. The calibration matrices resulting from the "offline" calibration are used in the fourth step in order to perform the first reconstruction.

The markers that are used on the patch are for example spherical markers in order to facilitate detection. They may also have shapes exhibiting rotational symmetry about axes of rotational symmetry.

The patch or patches containing the markers may be adhesively bonded directly to the patient or be positioned close to the area to be imaged.

In the case of adhesive patches, it is possible to use a patch defined as follows:

An adhesive tape that will be affixed to the skin of a patient or of an object, before the acquisition of the 2D images useful for reconstructing the 3D images, A set of radio-opaque markers distributed over the surface of the patch, An outer surface resistant to water, blood and friction, protecting the patch from its surroundings. The outer surface is for example made from plastic.

The self-adhesive patches may be single-use.

The markers are for example distributed so as to cover the entire surface of the patch.

The patch and markers assembly has for example a thickness of around 1 mm and an approximate size of 4×14 cm.

The markers may be integrated into a stretchable fabric or "medical stretch suit". The small markers, for example opaque beads, are for example distributed over the entirety of the compressive garment before covering the assembly to be reconstructed, part of the patient for example. It is then possible to simultaneously calibrate the device, using the information obtained in the fourth step, on the one hand, and reconstruct the envelope (3D surface) of the object to be reconstructed, on the other hand. This envelope will be used a priori for the 3D reconstruction.

According to one variant embodiment, the method will use one or more anatomical markers (characteristic and radio-opaque part of the human body) that correspond to points of interest present in an image. The markers will be extracted from the images using an image processing operation known to a person skilled in the art. In this variant embodiment, the method will not perform step 31 of positioning a patch. The first step will consist in acquiring X-ray images.

In some cases, it will be possible to associate markers contained in patches and anatomical markers, the latter being able to be implanted in the patient's body, for example in a bone.

The method according to the invention also makes it possible to calibrate a C-arm device using one or more markers, the position of these markers not being initially known.

The invention claimed is:

1. A method for calculating, during operation, a set of geometrical parameters of an X-ray imaging system, an object or a patient to be observed being positioned between an X-ray source and an X-ray detector detecting X-rays that have passed through the object or the patient, the object comprising a plurality of L markers, comprising at least the following steps for each marker $X_j$ affixed to the object or the patient:

using said marker $X_j$ having an initially unknown 3D position;

acquiring a plurality of 2D images for a plurality of viewpoints of the imaging system;

detecting the position $q_i$ of said marker $X_j$ in each of the acquired 2D images i; and estimating the projection matrices corresponding to the projections of the object at different viewing angles and reconstructing the position of said marker in 3D from the estimation of the projection matrices; and further comprising the step of iteratively estimating jointly X the set of said L 3D position of markers and M the set of N projection matrices while minimizing a criterion, the criterion being:

$$X, M = \mathrm{argmin}\, \Sigma_{i=1}^{N} \Sigma_{j=1}^{L} \|M_i X_j - q_{ij}\|.$$

2. The method as claimed in claim 1, comprising an offline calibration step in order to calculate the initial projection matrices.

3. The method as claimed in claim 1, wherein the initial projection matrices are calculated using at least one orientation sensor.

4. The method as claimed in claim 1, wherein the markers are contained in an adhesive patch positioned on or close to the patient or the object, defined as follows:

an adhesive tape, a set of radio-opaque markers distributed over the surface of the patch, a fluid-resistant outer surface.

5. The method as claimed in claim 1, wherein the markers are distributed on a patch so as to cover the entire surface of the patch.

6. The method as claimed in claim 1, wherein use is made of markers integrated into a stretchable fabric.

7. The method as claimed in claim 1, wherein use is made of small markers distributed over the entirety of a compressive garment before covering part of a patient to be reconstructed.

8. The method as claimed in claim 1, wherein use is made of at least one anatomical marker.

9. The method as claimed in claim 1, wherein use is made of at least one radio-opaque marker implanted in the patient's anatomy.

10. The method as claimed in claim 1, comprising a step of using geometrical features of the system in order to reconstruct a 3D image.

11. A device for calculating, during operation, the geometrical parameters of an X-ray imaging system, an object or a patient to be observed being positioned between the X-ray source and an X-ray detector detecting X-rays that have passed through the object or the patient, comprising at least one processing device comprising a processor configured to execute the steps of the method as claimed in claim 1.

12. The method as claimed in claim 1, wherein the initial projection matrices are calculated using one or more positioning sensors of the system.

\* \* \* \* \*

UNITED STATES PATENT AND TRADEMARK OFFICE
CERTIFICATE OF CORRECTION

PATENT NO. : 11,564,654 B2
APPLICATION NO. : 16/958894
DATED : January 31, 2023
INVENTOR(S) : Sébastien Gorges et al.

It is certified that error appears in the above-identified patent and that said Letters Patent is hereby corrected as shown below:

In the Claims

In Claim 1, Column 6, Line 51, "X, M =armgin $\sum_{i=1}^{N}\sum_{j=1}^{L} \|M_i X_j - q_{ij}\|$." should be
-- $X, M = argmin \sum_{i=1}^{N}\sum_{j=1}^{L} \|M_i X_j - q_{ij}\|$ --.

Signed and Sealed this
Eighteenth Day of April, 2023

Katherine Kelly Vidal
*Director of the United States Patent and Trademark Office*